(12) United States Patent
Maccecchini

(10) Patent No.: US 12,042,482 B2
(45) Date of Patent: Jul. 23, 2024

(54) METHODS OF TREATMENT OR PREVENTION OF ACUTE BRAIN OR NERVE INJURIES

(71) Applicant: ANNOVIS BIO, INC., Berwyn, PA (US)

(72) Inventor: Maria Maccecchini, West Chester, PA (US)

(73) Assignee: Annovis Bio, Inc., Berwyn, PA (US)

( * ) Notice: Subject to any disclaimer, the term of this patent is extended or adjusted under 35 U.S.C. 154(b) by 276 days.

(21) Appl. No.: 15/751,337

(22) PCT Filed: Aug. 12, 2016

(86) PCT No.: PCT/US2016/046794
§ 371 (c)(1),
(2) Date: Feb. 8, 2018

(87) PCT Pub. No.: WO2017/030968
PCT Pub. Date: Feb. 23, 2017

(65) Prior Publication Data
US 2018/0228771 A1  Aug. 16, 2018

Related U.S. Application Data

(60) Provisional application No. 62/205,431, filed on Aug. 14, 2015.

(51) Int. Cl.
| A61K 31/407 | (2006.01) |
| A61K 9/00 | (2006.01) |
| A61P 25/00 | (2006.01) |
| A61P 27/06 | (2006.01) |

(52) U.S. Cl.
CPC .......... *A61K 31/407* (2013.01); *A61K 9/0019* (2013.01); *A61K 9/0048* (2013.01); *A61K 9/0053* (2013.01); *A61P 25/00* (2018.01); *A61P 27/06* (2018.01)

(58) Field of Classification Search
CPC .. A61K 31/407; A61K 9/0019; A61K 9/0048; A61K 9/0053; A61P 25/00; A61P 27/06
USPC ........................................................ 514/411
See application file for complete search history.

(56) References Cited

U.S. PATENT DOCUMENTS

| 5,171,750 A | 12/1992 | Brossi et al. |
| 5,409,948 A | 4/1995 | Greig et al. |
| 6,410,747 B1 | 6/2002 | Greig et al. |
| 6,495,700 B1 | 12/2002 | Bruening et al. |
| 6,683,105 B2 | 1/2004 | Greig et al. |
| 7,153,882 B2 | 12/2006 | Greig et al. |
| 7,625,942 B2 | 12/2009 | Bruinsma et al. |
| 7,786,162 B2 | 8/2010 | Greig et al. |
| 7,994,210 B2 | 8/2011 | Bruinsma et al. |
| 8,258,172 B2 | 9/2012 | Greig et al. |
| 8,691,864 B2 | 4/2014 | Greig et al. |
| 2002/0094999 A1 | 7/2002 | Grieg et al. |
| 2005/0013869 A1 | 1/2005 | Chaw et al. |
| 2005/0182044 A1 | 8/2005 | Bruinsma |
| 2005/0272804 A1 | 12/2005 | Bruinsma |
| 2007/0037848 A1 | 2/2007 | Masters et al. |
| 2010/0298389 A1 | 11/2010 | Elmaleh et al. |
| 2011/0021594 A1 | 1/2011 | Grieg et al. |
| 2012/0225922 A1* | 9/2012 | Maccecchini ........ A61K 31/407 548/453 |

FOREIGN PATENT DOCUMENTS

| WO | WO 01/66114 A1 | 9/2001 |
| WO | WO0166114 | 9/2001 |
| WO | WO0248150 | 6/2002 |
| WO | WO03082270 | 10/2003 |
| WO | WO2004034963 | 4/2004 |
| WO | WO2005089746 | 9/2005 |
| WO | WO2005123068 | 12/2005 |
| WO | WO2010117727 | 10/2010 |
| WO | WO2012154285 | 11/2012 |
| WO | WO2010117727 | 10/2014 |
| WO | WO2017030968 | 2/2017 |

OTHER PUBLICATIONS

Maria L Maccecchini et al. Neurodegeneration, , J. Neural Neurosurg Psychiatry 2012, 83:894-902, Posiphen as a candidate drug to lower CSF amyloid precursor protein, amyloid-β peptide and τ levels: target engagement, tolerability and pharmacokinetics in humans).*
Debomoy Lahiri et al. (The Journal of Pharmacology and Experimental Therapeutics, vol. 320, No. 1, pp. 386-396, 2007.*
Vitoria Johnson et al. (Nat Rev Neurosci. May 2010; 11(5): 361-370).*
Hien T. Tran et al. (Controlled cortical impact traumatic brain injury in 3xTg-AD mice causes acute intra-axonal amyloid-β accumulation and independently accelerates the development of tau abnormalities. J Neurosci. Jun. 29, 2011;31(26):9513-25. doi: 10.1523/JNEUROSCI.0858-11.2011. PMID: 21715).*
Cullen et al. "Brain Beta-Amyloid 42 in Mice Treated Orally with Posiphen Tartrate is Significantly Lower than in Vehicle Controls," 9th International Geneva/Springfield Symposium on Advances in Alzheimer Therapy; (Apr. 19, 2006).
Holloway et al. "Mechanism of Action of Posiphen in CSF of mildly Cognitive Impaired Patients," QR Pharma, Inc., Radnor, PA.
(Continued)

*Primary Examiner* — Shobha Kantamneni
(74) *Attorney, Agent, or Firm* — Davidson Kappel LLC

(57) ABSTRACT

One of the aspects of the invention is directed toward a method of treating or preventing acute brain or nerve injury in a subject, comprising administering an effective amount of posiphen, or a pharmaceutically acceptable salt of posiphen, to the subject in need thereof. Similarly, another aspect of the invention is directed toward a use of posiphen, or a pharmaceutically acceptable salt of posiphen, for the treatment or prevention of acute brain or nerve injury. Preferably, the posiphen in the method or use of the invention is posiphen tartrate.

7 Claims, 4 Drawing Sheets

(56) References Cited

OTHER PUBLICATIONS

Soares et al., "Aβ Variability and Effects of Gamma Secretase Inhibition on Plasma and Cerebrospinal Fluid Levels of Aβ Peptide in Healthy Volunteers" Pfizer Global Research and Development, New London, CT.

Marutle et al. "Modulation of human neural stem cell differentiation in Alzheimer (APP23) transgenic mice by phenserine" The National Academy of Sciences of the USA; vol. 104, No. 30, pp. 12506-12511, (Jul. 24, 2007).

Brazzolotto et al., "Structural Changes Associated with Switching Activities of Human Iron Regulatory Protein 1*" The Journal of Biological Chemistry; vol. 277, No. 14, pp. 11995-12000, (2002).

Shaw et al., "Phenserine regulates translation of β-amyloid precursor protein mRNA by a putative interleukin-1 responsive element, a target for drug development" PNAS, vol. 98, No. 13; pp. 7605-7610, (Jun. 19, 2001).

Lahiri et al. "The Experimental Alzheimer's Disease Drug Posiphen [(+)-Phenserine] Lowers Amyloid-β Peptide Levels in Cell Culture and Mice" The Journal of Pharmacology and Experimental Therapeutics, vol. 320, No. 1; pp. 386-396; (2007).

Selkoe, "Defining Molecular Targets to Prevent Alzheimer Disease" American Medical Association; pp. 192-195; (2005).

Kadir et al. "Effect of Phenserine Treatment on Brain Functional Activity and Amyloid in Alzheimer's Disease" American Neurological Association, Wiley-Liss, Inc.; pp. 621-631; (2008).

Khachaturian, "Diagnosis of Alzheimer's Disease" Arch Neurology; vol. 42, pp. 1097; (Nov. 1985).

Cahill et al. "Amyloid Precursor Protein and Alpha Synuclein Translation, Implications for Iron and Inflammation in Neurodegenerative diseases" *Biochim Biophys Acta*. 1790(7): 615-628 (Jul. 2009).

Maccecchini et al. "Posiphen as a candidate drug to lower CSF amyloid precursor protein, amyloid-β peptide and τ levels: target engagement, tolerability and pharmacokinetics in humans" J Neurol Neurosurg Psychiatry; vol. 83; pp. 894-902; (2012).

Duce et al. "Iron-Export Ferroxidase Activity of β-Amyloid Precursor Protein is Inhibited by Zinc in Alzheimer's Disease" Cell; pp. 1-10; (2010), doi: 10.1016/j.cell.2010.08.014.

Kounnas et al. "Modulation of χ-Secretase Reduces β-Amyloid Deposition in a Transgenic Mouse Model of Alzheimer's Disease" Neuron; pp. 1-12; (2010).

Mikkilineni et al. "The Anticholinesterase Phenserine and Its Enantiomer Posiphen as 5' Untranslated-Region-Directed Translation Blockers of the Parkinson's Alpha Synuclein Expression" Hindawi Publishing Corporation; vol. 2012, Article ID 142372.

Venti et al. "The Integrated Role of Desferrioxamine and Phenserine Targeted to an Iron-Responsive Element in the APP-mRNA 5'-Untranslated Region" Ann. N.Y. Acad. Sci. vol. 1035: pp. 34-58 (2004).

Bandyopadhyay et al. "Novel 5' Untranslated Region Directed Blockers of Iron-Regulatory Protein-1 Dependent Amyloid Precursor Protein Translation: Implications for Down Syndrome and Alzheimer's Disease" PLOS One; vol. 8, Issue 7; pp. 1-14 (2013).

Maccecchini, "Targeting Alzheimer's with Novel Therapeutics" QR Pharma, Inc. Neuroscience Network; presented by Maria Maccecchini on May 11, 2010.

Harold W Holloway et al: "Posiphen and Analogs: Experimental Alzheimer' Agents that Reduce Amyloid-[beta] Peptide by Lowering Amyloid Precursor Protein Levels in Culture and In Vivo", 42nd Annual Winter Conference on Brain Research , Jan. 25, 2009 (Jan. 25, 2009) , 42nd Annual Winter Conference on Brain Research. Abstract only.

Maccecchini et al: "Targeting Alzheimer's with Novel Therapeutics", May 11, 2010 (May 11, 2010), Neuroscience Network, <<http:l/www.qrpharma.comlpdf/2010-5-11 Alzheimers Research Today Maria Maccecchini slides.pdf>>. Last accessed Jul. 22, 2014.

Maria L. Maccecchini: "Mechanism of Action of Posiphen : From Model to Human", Jan. 26, 2011 (Jan. 26, 2011) , 44nd Annual Winter Conference on Brain Research, <<http://wwwqrpharma.com/pdflWCBR Talk Jan. 2011.pdf>>. Last accessed Jul. 22, 2014.

Kadir et al: "Long-term effect of phenserine treatment in Alzheimer patients as assessed by PET and CSF biomarkers", Alzheimer's & Dementia the Journal of the Alzheimer's Association vol. 5, No. 4; p. 6.

Melo et al. Annals of the NY Academy of Sci., 1096, 1, 2007.

Maccecchini et al. (Poster presentations, Alzheimer's and Dementia, Jul. 2009, 5, 4, S1, p. 247-248).

Lahiri et al. (The J of Pharmacology and Experimental Therapeutics, 320, 1, 386-396, 2007).

Tomiyama, (The J of Biol. Chem, 271, 12, 6839-44, 1996).

Galvan, et al., "Reversal of Alzheimer's-like pathology and behavior in human APP transgenic mice by mutation of Asp664," PNAS, May 2, 2006, 103(18): pp. 7130-7135.

Nikolaev, et al., "APP binds DR6 to trigger axon pruning and neuron death via distinct caspases," Nature, Feb. 19, 2009, 457(19): pp. 981-990.

Takeda, et al., "Mechanisms ofNeuronal Death in Synucleinopathy," Journal ofBiomedicine and Biotechnology, 2006, vol. 2006, Article ID 19365, pp. 1-4.

Rogers, et al., "The alpha-synuclein 5'untranslated region targeted translation blockers: anti-alpha synuclein efficacy of cardiac glycosides and Posiphen," .1. Neural Transm, Oct. 15, 2010, DOI 10.1007/s00702-010-0513-5.

Cho, et al., "Selective Translational Control of the Alzheimer Amyloid Precursor Protein Transcript by Iron Regulatory Protein-1," Journal ofBiological Chemistry, Oct. 8, 2010, 285(41): pp. 31217-31232.

Khachaturian, "Diagnosis of Alzheimer's Disease," Arch Neural, Nov. 1985, 42: pp. 1097-1105.

International Search Report from International WIPO Publication No. WO 2012/154285 dated Aug. 17, 2012.

Maccecchini et al. "Posiphen lowers amyloid precursor protein and amyloid beta as well as acetylcholinesterase levels in culture, animals and humans" International Conference on Alzheimer's Disease; Jul. 12, 2009 (Abstract is retrieved from http://www.qrpharma.com/pdf/ICAD_Posiphen_06-30-2009.pdf on May 19, 2012; Publication date is retrieved from http://www/grpharma.com/pdf/WCBR_Posiphen_01%206%2009%20Poster.pdf on May 19, 2012) abstract, Figs. 1, 3, 4, 8(2).

Greig et al. "The experimental Alzheimer drug phenserine: preclinical pharmacokinetics and pharmacodynamics" Acta Neurol Scand 2000: Supplement 176: pp. 74-84.

Office Action from corresponding Korean Patent Application No. 10-2013-7025992 dated Jul. 30, 2018.

Janas et al. "The cholinesterase inhibitor, phenserine, improves Morris water maze performance of scopolamine-treated rats" Life Sciences, Pergamon Press, Oxford, GB, vol. 76, No. 10, (Jan. 21, 2005) pp. 1073-1081.

Pike et al. "Effect of tetrahydroaminoacridine, a cholinesterase inhibitor, on cognitive performance following experimental brain injury" Journal of Neurotrauma, vol. 14, No. 12, (Dec. 1997) pp. 897-905.

David et al. "Cognitive impairments Induced by Concussive Mild Traumatic Brain Injury in Mouse are Ameliorated by Treatment with Phenserine via Multiple Non-Cholinergic and Cholinergic Mechanisms" POLS One, vol. 11, No. 6, (Jun. 2, 2016) pp. e0156493.

International Search Report from International PCT Application No. PCT/US2016/046794 dated Feb. 23, 2017.

Hentze et al, "Two to Tango: Regulation of Mammalian Iron Metabolism" Cell. Jul. 9, 2010, vol. 142, No. 1, pp. 42-38; abstract; p. 26, $2^{nd}$ column, $4^{th}$ paragraph.

International Search Report from International PCT Application No. PCT/US18/34130 dated Sep. 4, 2018.

U.S Department of Health and Human Services Food and Drug Administration Center for Drug Evaluation and Research (CDER) "Guidance for Industry Estimating the Maximum Safe Starting Dose in Initial Clinical Trials for Therapeutics in Adult Healthy Volunteers"; Jul. 6, 2005.

Maccecchini et al. "Posiphen: Experimental Alzheimer Agent that Lowers Amyloid Precursor Protein Levels in Culture and In Vivo"; Dept. Psychiatry, Institute Psychiatric Research, Indiana Univ.,

(56) References Cited

OTHER PUBLICATIONS

Indianapolis, IN: Department of Neuroscience, Center of Aging, Medical University of S. Carolina, Charleston, SC;. PowerPoint Presentation. Dated Jan. 2011.

Summons to Attend Oral Proceedings mailed on Apr. 25, 2019 in connection to European Patent Application No. 12 782 326.8.

Anna M. Lija et al. "Neurotrophic and Neuroprotective Actions of (−)- and (+)-Phenserine, Candidate Drugs for Alzheimer's Disease" PLOS one; Jan. 2013, vol. 8, Issue 1.

Larson et al. (Annu. Rev. Publ. Health 13L431-49) (Year: 1992).

CAS Registry (1998, p. 1) (Year: 1998).

Phukan et al. (http://neurology.thelancet.com, vol. 6, Nov. 2007). (Year: 2007).

Klein (Phenserine, Expert Opin Investig. Drugs 2007, 16(7): 1087-1097 (Year: 2007).

Enright (https://louisaenright.com/2011 /11 /), 2011 (Year: 2011).

Novak et al. (Huntington's Disease, BMJ, Jul. 3, 2010). (Year: 2010).

\* cited by examiner

METHODS OF TREATMENT OR PREVENTION OF ACUTE BRAIN OR NERVE INJURIES

The present patent application concerns methods of treating or preventing acute brain or nerve injuries. The patent application claims the benefit of U.S. Provisional Patent Application No. U.S. 62/205,431, filed Aug. 14, 2015, the disclosures of which are incorporated by reference.

BACKGROUND

The functioning of the brain and nerves is sensitive to abnormal biochemical and/or structural changes. Abnormally low level of oxygen in the brain could adversely affect the brain function, and could even lead to structural injuries in the brain. As a result, the brain is very sensitive to any changes in the blood supply. For instance, an interruption, or reduction, of the blood supply to an area of the brain could lead to an infarct in the area and/or neuronal loss. The brain and nerves are also structurally fragile and are susceptible to structural damage upon violent physical impact. These injuries or damage to the brain and/or nerves are pathologically different from the chronic neurodegeneration associated with diseases such as Parkinson's disease and Alzheimer's disease. In terms of the temporal pattern, these injuries or damage to the brain and/or nerves are more acute than Parkinson's disease and Alzheimer's disease.

There are no drugs currently approved for the prevention or treatment of acute injuries to the brain and/or nerves. With sports and outdoor activities becoming more and more popular, and automobile accidents becoming more widespread, the incidence of acute brain or nerve injuries is higher than before. As acute brain or nerve injuries become more common, there is an increased need for a drug to prevent and/or treat acute injuries to the brain and/or nerves.

The present invention shows that posiphen is effective in the prevention or treatment of acute brain or nerve injuries. Posiphen has been known to be effective in preventing or treating neurotoxicity or neurodegenerative processes (US 2012/0225922A1). Posiphen has a chemical name of (3aR)-1,3a,8-trimethyl-1,2,3,3a,8,8a-hexahydropyrrolo[2,3-b]indol-5-yl phenylcarbamate. The chemical structure of posiphen is represented with Formula I.

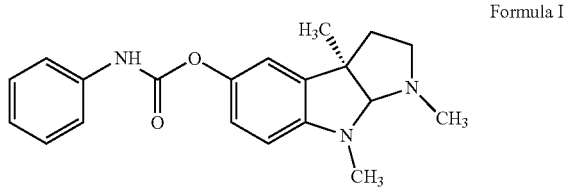 [SMILES: CN1CC[C@]2(C)c3cc(OC(=O)Nc4ccccc4)ccc3N(C)C12]

Formula I

SUMMARY OF THE INVENTION

The present invention is directed toward methods of treating or preventing an acute brain or nerve injury in a subject comprising administering an effective amount of posiphen, or a pharmaceutically acceptable salt of posiphen, to a subject in need thereof.

Similarly, the invention is directed to the use of posiphen, or a pharmaceutically acceptable salt of posiphen, for the treatment or prevention of an acute brain or nerve injury. Alternatively, the invention is directed to the use of posiphen, or a pharmaceutically acceptable salt of posiphen, in the manufacture of a medicine for the treatment or prevention of an acute brain or nerve injury.

DETAILED DESCRIPTION OF THE INVENTION

Figure 1:
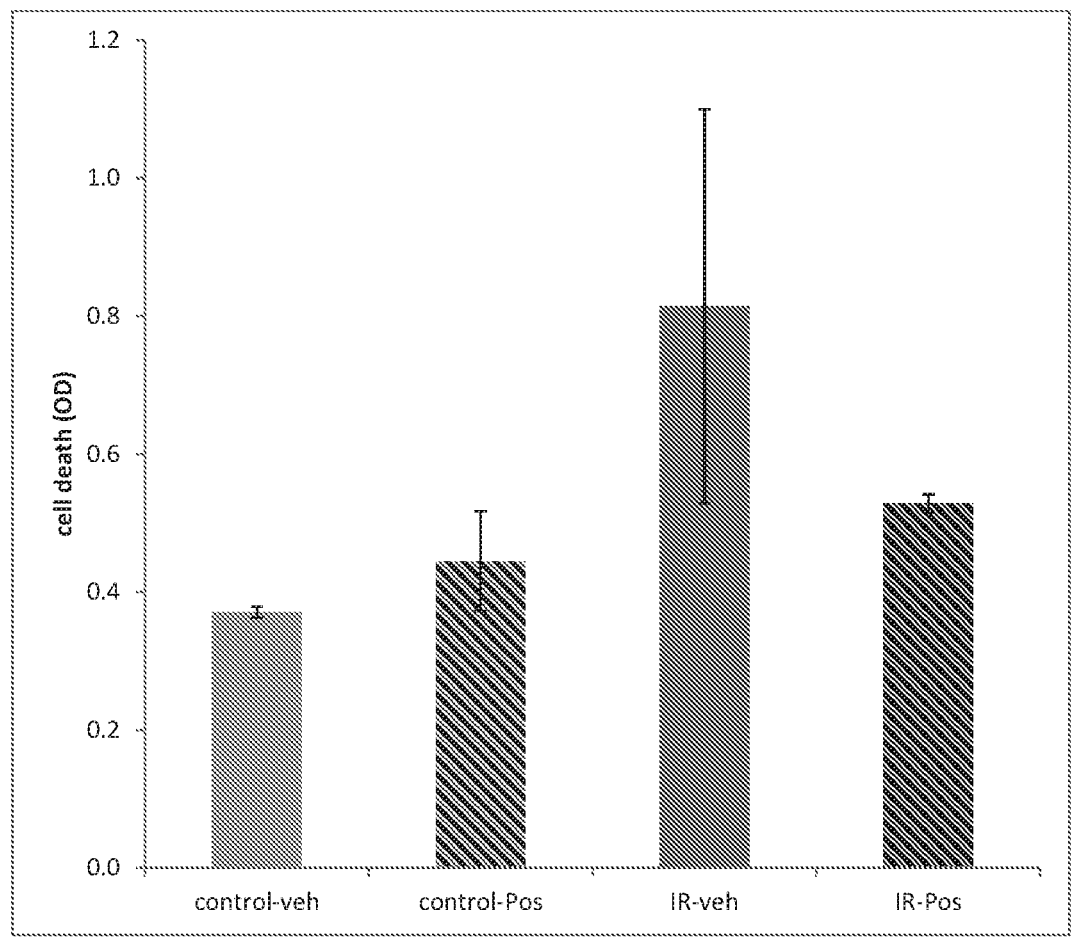
FIG. 1 shows the extent of dead nerve cells in the retina of an eye subjected to transient ischemia reperfusion (IR) and the retina of the opposite eye not subjected to IR (serving as the control) in two groups of rats: one group was treated with posiphen (the "IR-Pos" and "control-Pos") and the other group was treated with a vehicle (the "IR-veh" and "control-veh") in Example 1.

As used herein, the term "posiphen" refers to (3aR)-1,3a,8-trimethyl-1,2,3,3a,8,8a-hexahydropyrrolo[2,3-b]indol-5-yl phenylcarbamate, with the chemical structure shown in Formula I, at a chemical purity of at least 90%, preferably at least 95%, at least 98%, at least 990%, at least 99.5%, at least 99.9% or 100%.

The term "chemical purity" as applied to (3aR)-1,3a,8-trimethyl-1,2,3,3a,8,8a-hexahydropyrrolo[2,3-b]indol-5-yl phenylcarbamate or a pharmaceutically acceptable salt of posiphen means the percent by weight of (3aR)-1,3a,8-trimethyl-1,2,3,3a,8,8a-hexahydropyrrolo[2,3-b]indol-5-yl phenylcarbamate or the pharmaceutically acceptable salt of posiphen in terms of (3aR)-1,3a,8-trimethyl-1,2,3,3a,8,8a-hexahydropyrrolo[2,3-b]indol-5-yl phenylcarbamate or the pharmaceutically acceptable salt of posiphen and other chemical impurities, e.g., its (−)-enantiomer, that may be present.

Examples of the pharmaceutically acceptable salt of posiphen include acid addition salts prepared from a suitable acid. The suitable acid can be hydrobromic acid, hydrochloric acid, hydroiodic acid, sulfuric acid, carbonic acid, nitric acid, phosphoric acid, tetrafluoroboronic acid, perchloric acid, 1-hydroxy-2-naphthoic acid, 2,2-dichloroacetic acid, methanesulfonic acid, trifluoromethanesulfonic acid, 2-hydroxyethanesulfonic acid, benzenesulfonic acid, p-toluenesulfonic acid, cyclohexylaminosulfonic acid, 2-oxoglutaric acid, 4-acetamidobenzoic acid, acetic acid, phenylacetic acid, propionic acid, formic acid, succinic acid, glycolic acid, gluconic acid, malic acid, lactic acid, tartaric acid, citric acid, glucuronic acid, ascorbic acid, maleic acid, fumaric acid, pyruvic acid, aspartic acid, glutamic acid, benzoic acid, 4-hydroxybenzoic acid, anthranilic acid, 4-hydroxybenzoic acid, mandelic acid, pamoic acid, pantothenic acid, sulfanilic acid, stearic acid, alginic acid, β-hydroxybutyric acid, salicylic acid, galactaric acid and galacturonic acid. Preferably, the pharmaceutically acceptable salt is posiphen tartrate, i.e., the acid addition salt of tartaric acid.

Examples of the acute brain or nerve injury treated or prevented with the methods or uses of the invention include traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, e.g., falling out of windows, acute brain injury associated with physical impact of the head, and acute angle-closure glaucoma. The acute brain or nerve injury treated or prevented with the methods or uses of the invention excludes neurodegeneration associated with dementia of Alzheimer's disease, Parkinson's disease, Huntington's disease, Prion's disease, Amyloid Lateral Sclerosis, Tauopathy, Frontotemporal dementia, and chronic encephalopathy.

In the methods or uses of the invention, posiphen can be administered parenterally or enterally. Examples of the route of administration of posiphen are intravenous, intraocular, intramuscular, subcutaneous, topical, oral, sublingual and buccal. Preferably, posiphen is administered intravenously. For the treatment of acute angle-closure glaucoma, posiphen is preferably administered intraocularly or intravenously, with the intraocular route more preferred.

Posiphen, or a pharmaceutically acceptable salt of posiphen, can be administered once or repetitively. In the methods or uses of the invention for treating the acute brain or nerve injury, posiphen or a pharmaceutically acceptable salt of posiphen can be administered after an episode of the acute brain injury or acute angle-closure glaucoma has occurred. For example, in some of the embodiments of the methods or uses of the invention for treating the acute brain or nerve injury, posiphen or a pharmaceutically acceptable salt of posiphen can be administered once, twice, three times or four times within 24 hours after an episode of the acute brain injury or acute angle-closure glaucoma has occurred, starting as early as one minute, or within 0.5, 1, 1.5, 2, 3, 6, 12, 18, 20 or 22 hours after the episode of the acute brain or nerve injury such as acute angle-closure glaucoma has occurred. Posiphen, or a pharmaceutically acceptable salt of posiphen, can also be administered once, twice, three times or four times daily for up to one month after the episode of the acute brain injury or acute glaucoma has occurred. For instance, posiphen or a pharmaceutically acceptable salt of posiphen can be administered once, twice, three times or four times daily several days in a row, like 2, 3, 4, 5, 6 or 7 days, or daily for 2 or 3 weeks, or daily up to one month, after the episode of the acute brain injury or acute glaucoma has occurred. In the methods or uses of the invention to prevent the acute brain or nerve injury such as post-operative cognitive decline or a traumatic brain injury, posiphen or the pharmaceutically acceptable salt of posiphen is administered before an episode of the acute brain or nerve injury is expected to occur such as within 1 hour, 2 hours, 3 hours, 6 hours, 12 hours, 1 day, 2 days or 3 days before when the episode of the acute brain or nerve injury is expected to occur, for preventing the acute brain or nerve injury. For example, in some of the embodiments of the methods or uses of the invention for preventing the acute brain or nerve injury, posiphen or a pharmaceutically acceptable salt of posiphen can be administered once, twice, three times or four times within the first day, second day or third day before an episode of the acute brain injury or acute glaucoma occurs. In some of the embodiments of the methods or uses of the invention for preventing the acute brain or nerve injury, posiphen or a pharmaceutically acceptable salt of posiphen can be administered once, twice, three times or four times within the first day, and administered once, twice, three times or four times within the second day before an episode of the acute brain injury or acute glaucoma occurs. In some of the embodiments of the methods or uses of the invention for preventing the acute brain or nerve injury, posiphen or a pharmaceutically acceptable salt of posiphen can be administered once, twice, three times or four times within the first day, administered once, twice, three times or four times within the second day, and administered once, twice, three times or four times within the third day before an episode of the acute brain injury or acute glaucoma occurs.

Depending on the routes of administration, posiphen can be administered in different dose ranges. For example, in some of the embodiments of the methods or uses of the invention, posiphen is administered intravenously at 0.01 to 2 mg/kg body weight, preferably at 0.05 to 1 mg/kg, 0.05 to 0.5 mg/kg or 0.1 to 0.5 mg/kg body weight. In some of the embodiments of the methods or uses of the invention, posiphen is administered orally at 0.1 to 10 mg/kg body weight, preferably at 0.2 to 5 mg/kg body weight or 0.5 to 1 mg/kg body weight. In some of the embodiments of the methods or uses of the invention, posiphen is administered intraocularly at 0.001 to 0.2 mg/kg body weight, preferably at 0.002 to 0.1 mg/kg body weight, or 0.005 to 0.05 mg/kg body weight. When a pharmaceutically acceptable salt of posiphen is administered in a method or use of the invention, the appropriate dose of the pharmaceutically acceptable salt of posiphen administered can be calculated based on the dose of posiphen disclosed herein using the ratio of the molecular weight of posiphen and the molecular weight of the pharmaceutically acceptable salt of posiphen so that the amount of the pharmaceutically acceptable salt of posiphen administered would deliver a dose equivalent to the dose of posiphen disclosed herein.

In the methods or uses of the invention, the subject treated is a mammal, preferably a human. For example, the subject treated in the methods or uses of the invention is a mammal, or human, suffering from the acute nerve or brain injury.

The present invention includes the following embodiments.

Embodiment 1: A method of treating or preventing acute brain or nerve injury in a subject, comprising administering an effective amount of posiphen, or a pharmaceutically acceptable salt of posiphen, to the subject in need thereof.

Embodiment 2: The method according to Embodiment 1, wherein the posiphen, or a pharmaceutically acceptable salt of posiphen, administered to the subject is the pharmaceutically acceptable salt of posiphen.

Embodiment 3: The method according to Embodiment 2, wherein the pharmaceutically acceptable salt of posiphen is posiphen tartrate.

Embodiment 4: The method according to Embodiment 1, wherein posiphen or the pharmaceutically acceptable salt of posiphen administered to the subject has a chemical purity of at least 98%.

Embodiment 5: The method according to Embodiment 4, wherein posiphen or the pharmaceutically acceptable salt of posiphen administered to the subject has a chemical purity of at least 99%.

Embodiment 6: The method according to Embodiment 1, wherein the acute brain or nerve injury is traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, acute brain injury associated with physical impact of the head, or acute angle-closure glaucoma.

Embodiment 7: The method according to Embodiment 1, wherein the acute brain or nerve injury treated is an acute brain injury.

Embodiment 8: The method according to Embodiment 7, wherein the acute brain injury treated is traumatic brain injury, stroke, acute brain injury induced by brain ischemia, acute brain injury induced by insufficient oxygen supply to the brain, acute brain injury induced by anoxia or hypoxia, micro infarcts, acute brain injury induced by concussion, post-operative cognitive decline resulting from anesthesia or surgery-induced inflammation, acute brain injury induced by drowning, acute brain injury associated with whip lash, acute brain injury associated with bicycle crashes, acute brain injury associated with automobile accidents, shaken baby syndrome, acute brain injury induced by falling, or acute brain injury associated with physical impact of the head.

Embodiment 9: The method according to Embodiment 1, wherein the acute brain or nerve injury treated is an acute nerve injury.

Embodiment 10: The method according to Embodiment 9, wherein the acute nerve injury treated is acute angle-closure glaucoma.

Embodiment 11: The method according to Embodiment 1, wherein posiphen or the pharmaceutically acceptable salt of posiphen is administered intravenously.

Embodiment 12: The method according to Embodiment 10, wherein posiphen or the pharmaceutically acceptable salt of posiphen is administered intraocularly.

Embodiment 13: The method according to Embodiment 1, wherein posiphen is administered orally at a dose of 0.1 to 10 mg/kg body weight, or the pharmaceutically acceptable salt of posiphen is administered orally at a dose that is equivalent to a posiphen dose of 0.1 to 10 mg/kg body weight.

Embodiment 14: The method according to Embodiment 11, wherein posiphen is administered intravenously at a dose of 0.01 to 2 mg/kg body weight, or the pharmaceutically acceptable salt of posiphen is administered intravenously at a dose that is equivalent to a posiphen dose of 0.01 to 2 mg/kg body weight.

Embodiment 15: The method according to Embodiment 12, wherein posiphen is administered intraocularly at a dose of 0.001 to 0.2 mg/kg body weight, or the pharmaceutically acceptable salt of posiphen is administered intraocularly at a dose that is equivalent to a posiphen dose of 0.001 to 0.2 mg/kg body weight.

Embodiment 16: The method according to Embodiment 1, wherein posiphen or the pharmaceutically acceptable salt of posiphen is administered after an episode of the acute brain or nerve injury has occurred for treating the acute brain or nerve injury.

Embodiment 17: The method according to Embodiment 16, wherein posiphen or the pharmaceutically acceptable salt of posiphen is administered once, twice, three times or four times within 24 hours after the episode of the acute brain injury or acute angle-closure glaucoma has occurred, starting as early as one minute, or within 0.5, 1, 1.5, 2, 3, 6, 12, 18, 20 or 22 hours after the episode of the acute brain or nerve injury has occurred, or administered once, twice, three times or four times daily for up to one month after the episode of the acute brain injury or acute glaucoma has occurred.

Embodiment 18: The method according to Embodiment 1, wherein posiphen or the pharmaceutically acceptable salt of posiphen is administered before an episode of the acute brain or nerve injury is expected to occur such as within 1 hour, 2 hours, 3 hours, 6 hours, 12 hours, 1 day, 2 days or 3 days before the episode of the acute brain or nerve injury, for preventing the acute brain or nerve injury.

Embodiment 19: The method of Embodiment 18, wherein posiphen or a pharmaceutically acceptable salt of posiphen is administered once, twice, three times or four times within the first day, second day or third day before the episode of the acute brain or nerve injury occurs

EXAMPLES

Example 1

Prevention of Neuronal Cell Death in Retinal Ischemia-Reperfusion Posiphen was demonstrated to be effective in protecting the retina from neuronal cell death after transient ischemia-reperfusion (IR) in rats. IR is a well-established experimental model of glaucoma as well as neuronal cell death in other retinal diseases. IR was induced on one eye of each rat while the opposite eye served as an internal control. Transient IR was induced by raising the intraocular pressure by a controlled micro-injection of saline into the anterior chamber of the eye. This approach is well established to induce large amounts of apoptotic cell death in the retina, beginning within hours after the reperfusion and continuing for several days, leading to a loss of about 50% of the retina. There would also be a dramatic and persistent increase in the permeability of the vasculature of the inner retina during this period, which may lead to edema.

Adult male Sprague-Dawley rats (approx. 450 g, n=8) were housed under normal 12 hr light/dark conditions with free access to food and water. Rats were given posiphen tartrate (30 mg/kg body weight, delivered in 15 mg/ml water) or an equivalent volume of water (vehicle) by oral gavage once per day. Gavage was performed daily over three days and then on the fourth day IR was induced in anesthetized rats (ketamine:xylazine, 100:10 mg/kg, i.p.). IR was induced by slow injection of saline into the anterior chamber of the eye using a syringe pump (Harvard Instruments) which raised the intraocular pressure above that required for retinal perfusion, which rendered the retina ischemic (no blood flow, indicated by loss of the pink color of the fundus). The eye pressure was held constant for 50 min, followed by the removal of the cannulation needle which caused rapid reperfusion of the retina. The rats were sacrificed a further week later (14 days post IR). Retinas were rapidly dissected and snap frozen for storage. The retinas were homogenized and fractionated to obtain a cytoplasmic sample which was assessed for nucleosome content in duplicate, using the Cell Death ELISA (Roche). Data were averaged and expressed as optical density (OD).

Results: Retinal Cell Death Assay

The number of dead nerve cells in the retina of the eye subjected to transient IR and in the retina of the opposite eye (the control retina) in the rats treated with posiphen or the vehicle are shown in FIG. 1, wherein IR-veh was the eye subjected to transient IR in the rats administered with the vehicle; control-veh was the opposite eye in the rats administered with the vehicle; IR-Pos was the eye subjected to transient IR in the rats treated with posiphen; and control-Pos was the opposite eye in the rats treated with posiphen.

In the rats treated with the vehicle, approximately twice as many dead nerve cells were observed in the retina of the eye subjected to transient IR (IR-veh) than in the retina of the opposite eye not subjected to transient IR (control-veh). In contrast, in the rats treated with posiphen, the number of dead nerve cells in the retina of the eye subjected to transient IR (IR-Pos) was only slightly more than the number of dead nerve cells in the retina of the opposite eye not subjected to transient IR (control-Pos). Posiphen rescued 72% of the retinal neurons in the treated rats (IR-Pos). N=6. Thus, posiphen was effective in treating the acute nerve cell injury induced by the transient IR.

Example 2

Traumatic Brain Injury (TBI)

Figure 2:
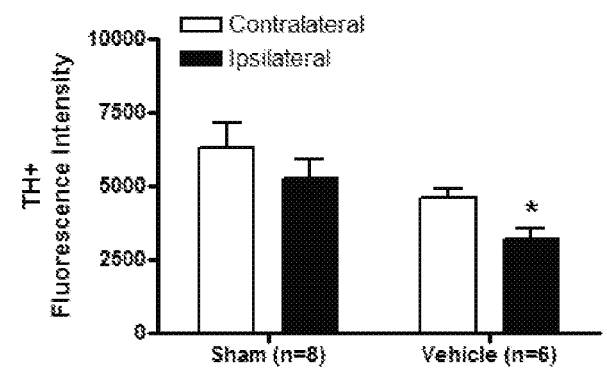
FIG. 2 shows the intensity of tyrosine hydroxylase (TH) immunoreactivity in the whole striatum of sham operated rats and rats subjected to fluid percussion injury (FPI) and treated with saline in Example 2, wherein the ipsilateral side was the side of the brain subjected to the fluid percussion injury in the rats treated with saline (the vehicle-treated group).
Figure 3:
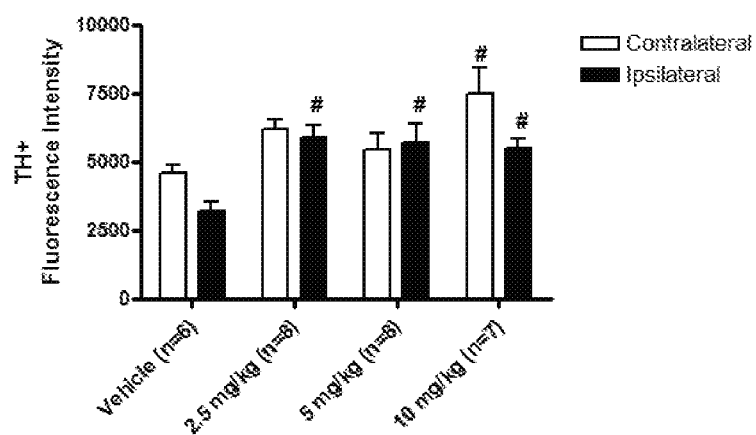
FIG. 3 shows the intensity of tyrosine hydroxylase (TH) immunoreactivity in the whole striatum of rats subjected to fluid percussion injury (FPI) treated with saline, posiphen at 2.5 mg/kg, posiphen at 5 mg/kg or posiphen at 10 mg/kg in Example 2, wherein the ipsilateral side was the side of the brain subjected to the fluid percussion injury.

Rats were subjected to fluid percussion injury (FPI) or sham operation to one side of the brain using the same procedures described in Griesbach et al (Brain Research, 1288:105-115, 2009; PMCID:PMC2735616) and Hutson et al (J. Neurotrauma, Jun. 6, 2011; PMID:21644813). The fluid percussion resulted in mild traumatic brain injury (TBI) in that side of the brain. About 5 to 30 minutes after FPI or sham operation, the rats were administered with saline or posiphen tartrate at a dose of 2.5, 5 or 10 mg/kg body weight intraperitoneally and also daily for the next 28 to 32 days. At 90 minutes after the last saline or posiphen treatment, all the rats were sacrificed and sections of the brain of each of the rats were stained for tyrosine hydroxylase (TH), wherein TH stains only live cells. The amounts of TH immunoreactivity in the whole striatum of the brain slices were measured. Stereological analysis of dopaminergic (DA) neurons in the substantia nigra was conducted to determine whether posiphen would block the TBI-induced loss of DA neurons ipsilateral and contralateral to the FPI injury, using procedures described in Johnson et al (Brain Pathol. Jun. 29, 2011, doi: 10.1111/j.1750-3639.2011.00513.x) and Hoshino et al (Neurol. Med. Chir. (Tokyo), 2003, April; 43(4): 165-74). The results are shown in FIGS. 2 and 3. The groups of rats included the rats with LOC above/at the median value. In FIG. 2, the sham operated group was compared with the vehicle group with two-way ANOVA, Bonferroni comparisons, wherein $*p<0.05$. In FIG. 3, the vehicle group was compared with the posiphen-treatment groups with one-way ANOVA, Bonferroni comparisons, wherein $\#p<0.05$.

Compared with the rats in the sham operated group, in the rats subjected to FPI in the vehicle group, a 25% death of the nerve cells in the contralateral area of the striatum and a 42% death in the ipsilateral area were detected, wherein the ipsilateral side was the side of the brain subjected to FPI. In the posiphen group, the rats treated with 3 doses of posiphen showed a statistically significant increase over the sham operated animals in the number of surviving cells in the ipsilateral area of the brain at all 3 doses and an increase in the number of nerve cells of the striatum in the contralateral part of the brain at the highest dose of 10 mg/kg. Posiphen protected the striatum in fluid percussion injury at all 3 doses tested.

The data are shown in FIGS. 2 and 3 as the mean+/− S.E.M. (standard error of the mean). A Student's t-test between the sham-operated group and vehicle-treated group revealed a significant decrease in TH+ fluorescence intensity in the striatum of the vehicle-treated group (t=2.470, $*p=0.0295$). Based on the data in the ipsilateral striatum (the ipsilateral side was the side of the brain subjected to FPI), posiphen treated animals showed full protection of the TH+ cells in all parts of the striatum (whole, rostral, medial and caudal). A one-way ANOVA with Bonferroni post-hoc comparisons revealed a significantly higher TH+ fluorescence intensity in all the posiphen-treated groups when compared with the vehicle-treated group (F=5.499, $\#p<0.05$). Posiphen attenuated the FPI-induced decrease in the TH+ terminals in the striatum.

Although no significant effect of the TBI on the TH+ fluorescent intensity was seen in any subregion of the substantia nigra, a very strong trend toward a decreased mean number of TH+ neurons in the ventral subregion was detected, when the data were analyzed with Student's t test, one tailed ($p=0.0^{59}$).

Example 3

Because FPI can induce microglial activation according to Hutson et al (J. Neurotrauma, Jun. 6, 2011; PMID: 21644813), whether posiphen would reverse this pathological response using quantitative measures was tested in the vehicle or posiphen tartrate treated (10 mg/kg) rats from Example 2 (part of the brain from each of the euthanized rat was stained for tyrosine hydroxylase in Example 2 and another part of the brain was stained for microglia in Example 3). Microglial activation was assessed by quantitative measure of the diameter of IBA-1-positive cells, wherein IBA-1 stands for ionized calcium adaptor binding protein. Microglia with cell body diameters less than 5 μm had a resting morphology characterized by multiple ramified processes. Hyper-ramified microglia/partially activated microglia had a mean cell body diameter of 5-6 μm. Fully activated amoeboid microglia had a mean cell body diameter of 7-14 μm, with an activated morphology characterized by ameboid cell bodies with few, short processes. Analysis was done on a Leica DM-LB microscope with a Ludl XYZ motorized stage and z-axis microcator (MT12, Heidenheim, Traunreut, Germany) using StereoInvestigator software (MicroBrightField, Colchester, VT). A contour was drawn to delineate the substantia nigra under the 5× objective lens to ensure anatomical accuracy. Following delineation, the diameters of microglial cell bodies were measured in the first counting frame (100 μm) and then in every fifth counting frame at 40× magnification. This sampling frequency was chosen in order to count approximately 30-50

Figure 4:
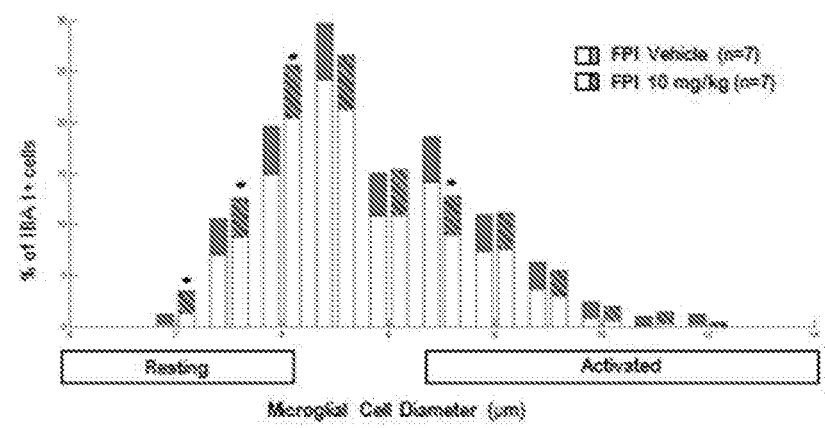
FIG. 4 shows the percentage of IBA-1$^+$ microglial cells in the substantia nigra of rats subjected to fluid percussion injury (FPI) and treated with saline (the vehicle), or posiphen at 10 mg/kg in Example 3, demonstrating that posiphen decreased brain inflammation after mild traumatic brain injury, wherein IBA-1$^+$ represents positive for ionized calcium adaptor binding protein. Data on the horizontal axis are diameters of IBA positive cell bodies in substantia nigra ipsilateral to the fluid percussion injury (FPI), an index of inflammation.

IBA-1+ cells in each side of the substantia nigra. The first counting frame was always positioned in the upper left corner of the contour and systematically moved from left to right and from top to bottom until the entire delineated contour region was sampled. The number of IBA-1+ microglia cells with cell diameters ranging from 1 μm to 14 μm was then normalized to the total number counted in each section and expressed as a percentage of total microglia. The results are shown in FIG. 4 (wherein the percent of IBA-1+ cells was plotted on the vertical axis, and the microglial cell diameter in μm was plotted on the horizontal axis). In FIG. 4, the blank portion of each data bar represents the mean % of IBA-1+ cells with the solid or striped portion at the top of the bar representing the 95% confidence interval. In each pair of data bars in FIG. 4, the bar on the left having a solid portion at the top represents data from the vehicle-treated group, while the bar on the right having a striped portion at the top represents data from the 10 mg/kg posiphen-treated group, wherein the data of the posiphen-treated group (the bar on the right) were compared with the data of the vehicle-treated group (the bar on the left) with Bootstrapping method. The asterisks (*) at the top of some of the bars of the 10 mg/kg posiphen-treated group indicate statistical significance at p<0.05 when compared with the data of the corresponding bar of the vehicle-treated group as analyzed with the Bootstrapping method. Posiphen increased the number of resting microglia and reduced the number of activated microglia.

The data show that FPI increased microglia activation in the substantia nigra ipsilateral to the injury, an effect attenuated by posiphen at a dose of 10 mg/kg in a statistically significant manner. The diameters of IBA positive cell bodies in substantia nigra ipsilateral to the injury were an index of inflammation. The data show that posiphen decreased brain inflammation after traumatic brain injury.

Example 4

The objective of this example was to establish the efficacy of posiphen as a treatment of traumatic brain injuries (TBIs). In a mild model of TBI, posiphen was shown to improve water maze performance in rats subjected to TBI as described below.

Posiphen Improved Performance of Working Memory in Morris Water Maze

Figure 5:
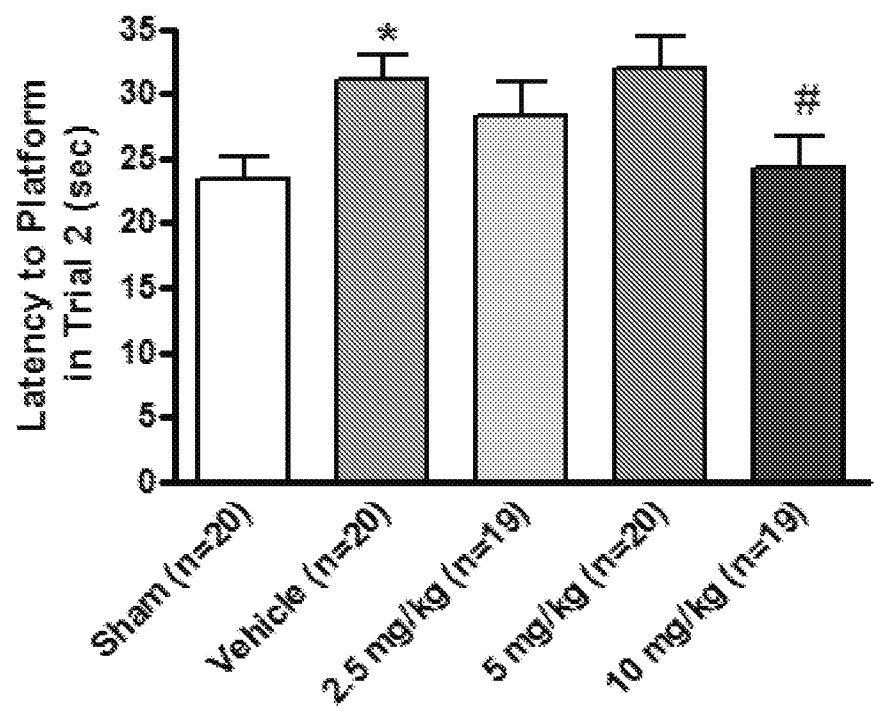
FIG. 5 shows the latency for rats to reach a platform in a Morris water maze in Example 4. The rats were subjected to mild traumatic brain injury and were divided into sham-operated group, vehicle-treated group, and posiphen-treated groups at a dose of 2.5 mg/kg of body weight, 5 mg/kg of body weight or 10 mg/kg of body weight.

The vehicle or posiphen tartrate treated rats from Example 2 were also subjected to working memory test in Morris water maze. Each of the rats was individually tested in the Morris water maze, which had 4 release points for putting the rat into the water and 4 platforms for the rat to swim to. For a total of 3 consecutive days (on one and two days before the last vehicle or posiphen treatment, and also on the day of the last vehicle or posiphen treatment before euthanasia), the rats were tested on their ability to find the 4 platform positions, using paired trials (4 paired trials per day). In each pair of the trials, the first trial was the learning trial, for the rat to learn the position of a platform, and the second trial was the memory trial for testing the memory of the rat to swim to the platform that the rat learned in the learning trial. In the learning trial, each of the rats was allowed a maximum swim time of 90 seconds to swim to the platform, and guided to the platform if needed after 90 seconds. The memory trial was started 5 seconds after the completion of the learning trial and the time for the rat to reach the platform by swimming in the maze in the memory trial was recorded. The 4 platform positions were switched after every pair of trials. The time interval between the learning trials of two consecutive pairs of trials in a day was 5 minutes. The data were averaged over the 3 days. The mean duration of time (and +/−standard error of the mean) for 5 groups of the rats to reach the platform in the memory trials in the Morris water maze are shown in FIG. 5. Based on a one-way ANOVA with Bonferroni post-hoc comparisons between the vehicle-treated group and 10 mg/kg posiphen-treated group (depicted with the bar marked with the # symbol), a statistically significant difference was found (t=2.209 and p=0.0335). The other two posiphen doses, 2.5 mg/kg and 5 mg/kg, revealed a non-significant trend toward a reduction in latency to find the platform (F=2.192; p=0.0961). Thus, posiphen at a dose of 10 mg/kg rescued FPI injury-induced impairment as tested in the working memory Morris water maze.

The experiment showed a significant decrease in performance in the vehicle-treated group when compared to the sham group indicating that the FPI induced a performance deficit in the vehicle-treated rats as tested with the working memory Morris water maze. The experiment also showed an amelioration of this deficit in the 10 mg/kg posiphen group when compared to the vehicle-treated group.

The invention claimed is:

1. A method of treating an acute brain or acute nerve injury in a human subject, consisting of administering an effective amount of posiphen, or a pharmaceutically acceptable salt of posiphen intravenously, intramuscularly, subcutaneously, intraperitoneally, topically, orally, sublingually or buccally, to a human subject prior to the human subject experiencing the acute brain or acute nerve injury in order to reduce nerve cell death, wherein the posiphen or pharmaceutically acceptable salt thereof is administered within about 3 days before an episode of the acute brain or nerve injury and is thereafter administered for at least 7 days, and wherein posiphen or a pharmaceutically acceptable salt of posiphen is administered once, twice, three times or four times within the first day, second day or third day before the episode of the acute brain or acute nerve injury occurs, wherein the acute brain or acute nerve injury is traumatic brain injury.

2. The method according to claim 1, wherein the episode of acute brain injury is associated with physical impact of the head.

3. The method according to claim 2, wherein the pharmaceutically acceptable salt of posiphen is posiphen tartrate.

4. The method according to claim 1, wherein posiphen or the pharmaceutically acceptable salt of posiphen is administered intravenously.

5. The method according to claim 1, wherein posiphen is administered orally at a dose of 0.1 to 10 mg/kg body weight, or the pharmaceutically acceptable salt of posiphen is administered orally at a dose that is equivalent to a posiphen dose of 0.1 to 10 mg/kg body weight.

6. The method according to claim 4, wherein posiphen is administered intravenously at a dose of 0.01 to 2 mg/kg body weight, or the pharmaceutically acceptable salt of posiphen is administered intravenously at a dose that is equivalent to a posiphen dose of 0.01 to 2 mg/kg body weight.

7. The method according to claim 1, wherein posiphen or the pharmaceutically acceptable salt of posiphen is administered intramuscularly or intraperitoneally.

* * * * *